(12) United States Patent
Suga et al.

(10) Patent No.: US 11,045,154 B2
(45) Date of Patent: Jun. 29, 2021

(54) ROBOTIC OPERATING TABLE AND HYBRID OPERATING SYSTEM

(71) Applicant: MEDICAROID CORPORATION, Kobe (JP)

(72) Inventors: Kazunori Suga, Kobe (JP); Tetsuya Nakanishi, Kobe (JP)

(73) Assignee: MEDICAROID CORPORATION, Kobe (JP)

( * ) Notice: Subject to any disclaimer, the term of this patent is extended or adjusted under 35 U.S.C. 154(b) by 303 days.

(21) Appl. No.: 15/855,909

(22) Filed: Dec. 27, 2017

(65) Prior Publication Data

US 2018/0177470 A1 Jun. 28, 2018

(30) Foreign Application Priority Data

Dec. 28, 2016 (JP) .............................. JP2016-255014
Oct. 11, 2017 (JP) .............................. JP2017-197347

(51) Int. Cl.

| A61B 6/04 | (2006.01) |
|---|---|
| A61G 13/04 | (2006.01) |
| A61B 5/00 | (2006.01) |
| A61G 13/06 | (2006.01) |
| A61G 13/02 | (2006.01) |

(Continued)

(52) U.S. Cl.
CPC ............ *A61B 6/0407* (2013.01); *A61B 5/055* (2013.01); *A61B 5/704* (2013.01); *A61B 6/0487* (2020.08); *A61B 6/4417* (2013.01); *A61G 13/02* (2013.01); *A61G 13/04* (2013.01); *A61G 13/06* (2013.01); *A61B 6/0442* (2013.01); *A61G 2210/50* (2013.01)

(58) Field of Classification Search
CPC ..... A61B 6/0407; A61B 6/0457; A61B 5/704; A61B 5/0555; A61B 34/30; A61B 2090/376; A61B 2090/374; A61B 90/37; A61B 6/0442; A61G 13/06; A61G 13/04; A61G 2210/50; A61G 13/10; A61G 13/02; A61N 5/1049; B25J 9/00

USPC .............................................................. 5/601
See application file for complete search history.

(56) References Cited

U.S. PATENT DOCUMENTS 2,522,759 A * 9/1950 Lindquist ............... A61G 7/005
5/610
3,754,749 A * 8/1973 Lyon .................... A61G 13/009
5/618

(Continued)

FOREIGN PATENT DOCUMENTS

| JP | 2009-131718 A | 6/2009 |
|---|---|---|
| WO | 9742876 A1 | 11/1997 |

OTHER PUBLICATIONS

Pavan Nishad, "What is Double Reduction Gearing", (Jan. 14, 2013), Quora, p. 1—FIG. 1 (Year: 2013).*

*Primary Examiner* — Nicholas F Polito
*Assistant Examiner* — Luke Hall
(74) *Attorney, Agent, or Firm* — Metrolex IP Law Group, PLLC

(57) ABSTRACT

An operating table may include: a table on which to place a patient; a base buried or fixed to a floor; and an articulated robotic arm including first end supported on the base and a second end supporting the table, wherein the robotic arm includes at least one vertical joint, and a rotation axis of the vertical joint is positioned along a direction that is horizontal and substantially parallel to the longitudinal direction of the table.

16 Claims, 8 Drawing Sheets

(51) Int. Cl.
  *A61B 6/00*  (2006.01)
  *A61B 5/055*  (2006.01)

(56) References Cited

U.S. PATENT DOCUMENTS

| | | | | |
|---|---|---|---|---|
| 5,149,074 A * | 9/1992 | Jarin | A61B 6/04 | 5/601 |
| 5,230,112 A * | 7/1993 | Harrawood | A61G 13/10 | 5/607 |
| 5,337,627 A * | 8/1994 | Nakamura | F16H 25/2204 | 74/424.76 |
| 5,398,356 A * | 3/1995 | Pfleger | A61B 6/04 | 5/601 |
| 5,410,767 A * | 5/1995 | Barud | A61B 6/04 | 108/143 |
| 6,502,261 B1 * | 1/2003 | Harwood | A61G 13/02 | 5/611 |
| 6,507,964 B1 * | 1/2003 | Lewandowski | A61G 7/012 | 5/600 |
| 6,681,423 B2 * | 1/2004 | Zachrisson | A61G 13/04 | 5/601 |
| 7,860,550 B2 * | 12/2010 | Saracen | A61B 6/548 | 600/410 |
| 8,126,114 B2 * | 2/2012 | Naylor | A61B 34/30 | 378/65 |
| 8,160,205 B2 * | 4/2012 | Saracen | A61B 6/0457 | 378/35 |
| 8,740,880 B2 * | 6/2014 | Pinault | A61N 5/1049 | 606/1 |
| 8,904,582 B2 * | 12/2014 | Bergfjord | A61G 13/06 | 5/601 |
| 9,326,907 B2 * | 5/2016 | Marle | A61G 7/1057 | |
| 2002/0156365 A1 * | 10/2002 | Tsekos | A61B 5/0555 | 600/411 |
| 2005/0234327 A1 * | 10/2005 | Saracen | A61B 6/548 | 600/407 |
| 2007/0162152 A1 * | 7/2007 | Herr | A61F 2/60 | 623/24 |
| 2008/0301872 A1 * | 12/2008 | Fahrig | A61B 6/0457 | 5/81.1 R |
| 2009/0070936 A1 * | 3/2009 | Henderson | B25J 9/1676 | 5/601 |
| 2011/0066278 A1 * | 3/2011 | Pinault | A61N 5/1049 | 700/213 |
| 2011/0067946 A1 * | 3/2011 | Kim | B62D 5/0409 | 180/444 |
| 2013/0008276 A1 * | 1/2013 | Horikawa | F16H 55/088 | 74/427 |
| 2013/0046409 A1 * | 2/2013 | Tanaka | B25J 9/103 | 700/258 |
| 2013/0111666 A1 * | 5/2013 | Jackson | A61G 13/0036 | 5/601 |
| 2013/0336449 A1 * | 12/2013 | Tanabe | A61N 5/1067 | 378/62 |
| 2014/0033432 A1 * | 2/2014 | Marle | A61B 6/0487 | 5/601 |
| 2014/0034061 A1 * | 2/2014 | Marle | A61B 6/4494 | 128/845 |
| 2015/0059095 A1 * | 3/2015 | Bergfjord | A61N 5/1069 | 5/611 |
| 2015/0135438 A1 * | 5/2015 | Marugg | A61G 13/04 | 5/608 |
| 2015/0327818 A1 * | 11/2015 | Buck | A61B 6/0457 | 5/608 |
| 2016/0000620 A1 * | 1/2016 | Koch | A61G 7/008 | 5/608 |
| 2017/0156684 A1 * | 6/2017 | Van De Rijdt | A61B 6/04 | |
| 2018/0085603 A1 * | 3/2018 | Kruesi | A61B 5/0555 | |

* cited by examiner

ROBOTIC OPERATING TABLE AND HYBRID OPERATING SYSTEM

CROSS REFERENCE TO RELATED APPLICATIONS

This application claims priority based on 35 USC 119 from prior Japanese Patent Applications No. 2016-255014 filed on Dec. 28, 2016, and No. 2017-197347 filed on Oct. 11, 2017, entitled "ROBOTIC OPERATING TABLE AND HYBRID OPERATING ROOM", the entire contents of which are incorporated herein by reference.

BACKGROUND

This disclosure relates to a robotic operating table and a hybrid operating system.

A patient positioning assembly has heretofore been known which uses a robotic arm to move a table with a patient placed thereon and position the patient relative to a treatment radiation source (see Japanese Patent Application Publication No. 2009-131718 (Patent Literature 1), for example).

Meanwhile, there has heretofore been a demand for an operating table that allows a table with a patient placed thereon to be easily moved while preventing interference with surrounding equipment in an operating room. To this end, one may consider applying the patient positioning assembly of Patent Literature 1 mentioned above to an operating table in an operating room to move the table with a patient placed thereon by using the robotic arm. In this way, the table with the patient placed thereon can be easily moved while being prevented from interfering with surrounding equipment, unlike cases where an operating table is moved using casters.

SUMMARY

Since patient positioning assemblies as described in Patent Literature 1 mentioned above are intended for irradiation of the patient with treatment radiation, they do not need to consider situations where staff work for a long time around the table with the patient placed thereon, and typically use a large robotic arm. For this reason, if applied to an operating table, the robotic arm of Patent Literature 1 reduces the space around the operating table and may interfere with medical personnel during surgical operations. In a case where a robotic arm including joints is downsized to prevent it from obstructing surgical operations, the joints are reduced in size as well, which leads to a disadvantage that the strength of the joints to withstand loads thereon is lowered. Vertical joints that vertically move a table may be subjected to a large moment load especially when vertically moving the table with a heavy patient placed thereon. This leads to a problem that it is difficult to downsize a robotic arm to prevent it from obstructing surgical operations.

One or more embodiments of a robotic operating table is capable of downsizing an articulated robotic arm that moves a table on which to place a patient on whom a surgical operation is to be performed, while ensuring that a vertical joint of the articulated robotic arm has strength to withstand loads thereon.

A robotic operating table according to a first aspect of one or more embodiments include a table on which to place a patient; a base buried or fixed to a floor; and an articulated robotic arm including a first end supported on the base and the second end supporting the table. The articulated robotic arm includes at least one vertical joint, and the rotation axis of the vertical joint is positioned along a direction that is horizontal and substantially parallel to the longitudinal direction of the table.

A robotic operating table according to a second aspect of one or more embodiments include a table on which to place a patient; a base buried or fixed to a floor; and an articulated robotic arm including a first end supported on the base and the second end supporting the table. The articulated robotic arm includes vertical joints, and the rotation axis of each of the vertical joints is positioned along a direction that is horizontal and substantially parallel to the longitudinal direction of the table.

A hybrid operating system according to a third aspect of one or more embodiments include at least one of a radiographic imaging apparatus that captures a radiographic projection image of a patient and a magnetic resonance imaging apparatus that captures a magnetic resonance image of a patient and an operating table including a table on which to place a patient, a base buried or fixed to a floor, and an articulated robotic arm including a first end supported on the base and a second end supporting the table. The articulated includes at least one vertical joint, and the rotation axis of the vertical joint is disposed along a direction that is horizontal and substantially parallel to a longitudinal direction of the table.

DETAILED DESCRIPTION

Figure 1:
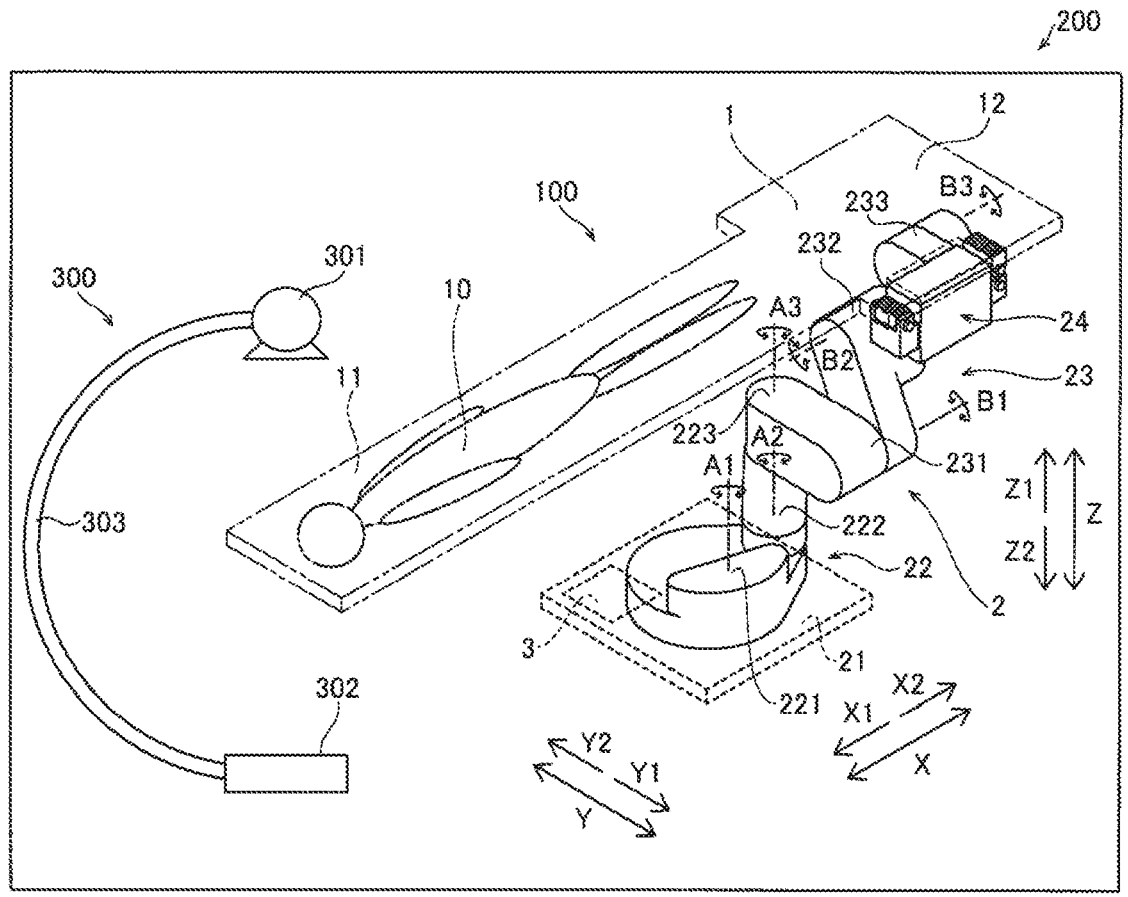
FIG. 1 is a view illustrating an overview of a hybrid operating system including a robotic operating table according to a first embodiment.

Embodiments are described with reference to drawings, in which the same constituents are designated by the same reference numerals and duplicate explanation concerning the same constituents may be omitted for brevity and ease of explanation. The drawings are illustrative and exemplary in nature and provided to facilitate understanding of the illustrated embodiments and may not be exhaustive or limiting. Dimensions or proportions in the drawings are not intended to impose restrictions on the disclosed embodiments. For this reason, specific dimensions and the like should be interpreted with the accompanying descriptions taken into consideration. In addition, the drawings include parts whose dimensional relationship and ratios are different from one drawing to another.

Prepositions, such as "on", "over" and "above" may be defined with respect to a surface, for example a layer surface, regardless of the orientation of the surface in space.

First Embodiment (Configuration of Robotic Operating Table)

An overview of a robotic operating table 100 according to a first embodiment is explained with reference to FIG. 1 to FIG. 9.

As illustrated in FIG. 1, the robotic operating table 100 is provided in a hybrid operating system 200. The hybrid operating system 200 is provided with a radiographic imaging apparatus 300 that captures a radiographic projection images of a patient 10. A hybrid operating system provided in the hybrid operating system 200 includes a robotic operating table 100 and the radiographic imaging apparatus 300. The robotic operating table 100 is used as a table for operations performed in a setting such as a surgery or internal medicine setting. The robotic operating table 100 is capable of moving a table 1 to a placement position at which to place the patient 10 onto the table 1, and moving the patient 10 to an anesthetization position, a surgical operation position, an examination position, a treatment position, a radiographic imaging position, and so on while the patient 10 is placed on the table 1. Also, the robotic operating table 100 is capable of tilting the patient 10 while the patient 10 is placed on the table 1.

The robotic operating table 100 includes the table 1, on which to place the patient, an articulated robotic arm 2, and a control unit 3. The table 1 includes a radiolucent part 11 and a support part 12. The articulated robotic arm 2 includes a base 21, a horizontal articulated assembly 22, a vertical articulated assembly 23, and a pitch mechanism 24. The horizontal articulated assembly 22 includes horizontal joints 221, 222, and 223. The vertical articulated assembly 23 includes vertical joints 231, 232, and 233. The radiographic imaging apparatus 300 includes an X-ray irradiation part 301, an X-ray detection part 302, and a C-arm 303.

As illustrated in FIG. 1, the table 1 is formed in the shape of a substantially rectangular flat plate. Also, the upper surface of the table 1 is formed to be substantially flat. The table 1 has its longitudinal direction along an X direction and its transverse direction along a Y direction. Note that, while the table 1 is rotatable about an axis along the vertical direction (Z direction), the horizontal direction along the longitudinal direction of the table 1 is defined as the X direction and the horizontal direction along the transverse direction of the table 1 is defined as the Y direction here. In other words, the X direction and the Y direction represent directions based on the table 1.

As illustrated in FIG. 1, the patient 10 is placed on the radiolucent part 11 of the table 1. The radiolucent part 11 is disposed on the X1 direction side. The radiolucent part 11 is formed in a substantially rectangular shape. The radiolucent part 11 is made of a radiolucent material. The radiolucent part 11 is made of a carbon material (graphite), for example. The radiolucent part 11 is made of a carbon fiber reinforced plastic (CFRP), for example. In this way, a radiographic image of the patient 10 can be captured while the patient 10 is placed on the radiolucent part 11.

The support part 12 of the table 1 is connected to the articulated robotic arm 2. The support part 12 is disposed on the X2 direction side. The support part 12 is formed in a substantially rectangular shape. The support part 12 supports the radiolucent part 11. The support part 12 is made of a material smaller in radiolucency than the radiolucent part 11. The support part 12 is made of metal, for example. The support part 12 is made of a steel material or an aluminum material, for example.

The table 1 is moved by the articulated robotic arm 2. Specifically, the table 1 is movable in the X direction, which is a horizontal direction, in the Y direction, which is the horizontal direction perpendicular to the X direction, and in the Z direction, which is perpendicular to the X direction and the Y direction and is the vertical direction. Moreover, the table 1 is rotatable (capable of being caused to roll) about an axis along the X direction. The table 1 is also rotatable (capable of being caused to pitch) about an axis along the Y direction. The table 1 is also rotatable (capable of being caused to yaw) about an axis along the Z direction.

The articulated robotic arm 2 moves the table 1. As illustrated in FIG. 1, one end of the articulated robotic arm 2 is supported on the base 21, which is fixed to the floor, while the opposite end supports the table 1 such that the articulated robotic arm 2 can move the table 1. Specifically, the articulated robotic arm 2 is supported on the base 21 such that the articulated robotic arm 2 is rotatable about an axis along the vertical direction (Z direction). Also, the articulated robotic arm 2 supports the table 1 at a position near its one end on the X2 direction side in the longitudinal direction (X direction). In other words, the opposite end of the articulated robotic arm 2 supports the support part 12, which is situated on the one end side of the table 1.

The articulated robotic arm 2 moves the table 1 with seven degrees of freedom. Specifically, with the horizontal articulated assembly 22, the articulated robotic arm 2 has three degrees of freedom to rotate about a vertical rotation axis A1, rotate about a vertical rotation axis A2, and rotate about a vertical rotation axis A3. Further, with the vertical articulated assembly 23, the articulated robotic arm 2 has three degrees of freedom to rotate about a horizontal rotation axis B1, rotate about a horizontal rotation axis B2, and rotate about a horizontal rotation axis B3. Furthermore, with the pitch mechanism 24, the articulated robotic arm 2 has one degree of freedom to allow the table 1 to pitch about a rotation axis along its transverse direction (Y direction) (see FIG. 8 and FIG. 9).

As illustrated in FIG. 1, the base 21 is buried in and fixed to the floor. The base 21 is provided substantially at the center of the range of movement of the table 1 in a plan view (as seen from the Z direction).

Figure 2:
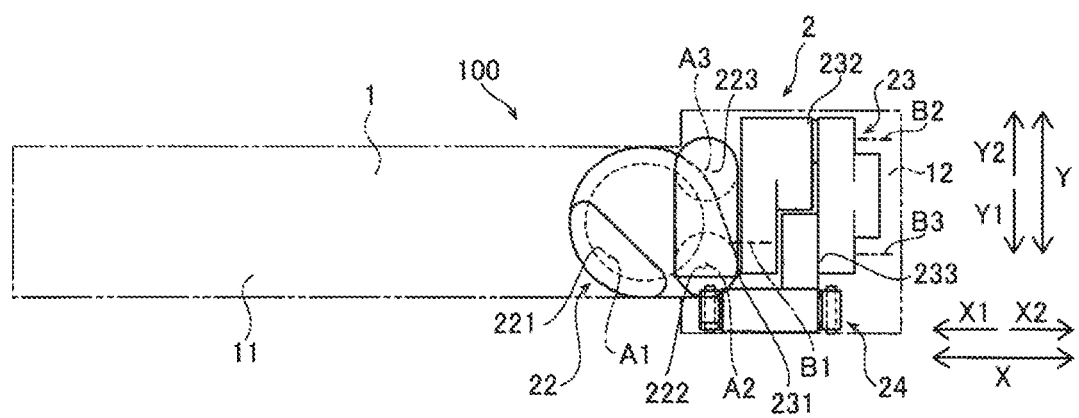
FIG. 2 is a plan view of the robotic operating table according to the first embodiment.

As illustrated in FIG. 1 and FIG. 2, one end of the horizontal articulated assembly 22 is supported on the base 21. Moreover, the opposite end of the horizontal articulated assembly 22 supports one end of the vertical articulated assembly 23. The horizontal joint 221 of the horizontal articulated assembly 22 rotates about the rotation axis A1 along the Z-direction. The horizontal joint 222 of the horizontal articulated assembly 22 rotates about the rotation axis A2 along the Z-direction. The horizontal joint 223 of the horizontal articulated assembly 22 rotates about the rotation axis A3 along the Z-direction.

As illustrated in FIG. 1 and FIG. 2, the one end of the vertical articulated assembly 23 is supported on the horizontal articulated assembly 22. Moreover, the opposite end of the vertical articulated assembly 23 supports the table 1. Specifically, the opposite end of the vertical articulated assembly 23 supports the table 1 through the pitch mechanism 24. The vertical joint 231 of the vertical articulated assembly 23 rotates about the rotation axis B1 along the X-direction. The vertical joint 232 of the vertical articulated assembly 23 rotates about the rotation axis B2 along the X-direction. The vertical joint 233 of the vertical articulated assembly 23 rotates about the rotation axis B3 along the X-direction.

The distance between each pair of adjacent joints has a length shorter than the length of the table 1 in the transverse direction (Y direction). Specifically, the distance between the rotation axis A1 and the rotation axis A2, the distance between the rotation axis A2 and the rotation axis A3, the distance between the rotation axis A3 and the rotation axis B1, the distance between the rotation axis B1 and the rotation axis B2, and the distance between the rotation axis B2 and the rotation axis B3 each have a length shorter than the length L3 of the table 1 in the transverse direction.

Figure 3:
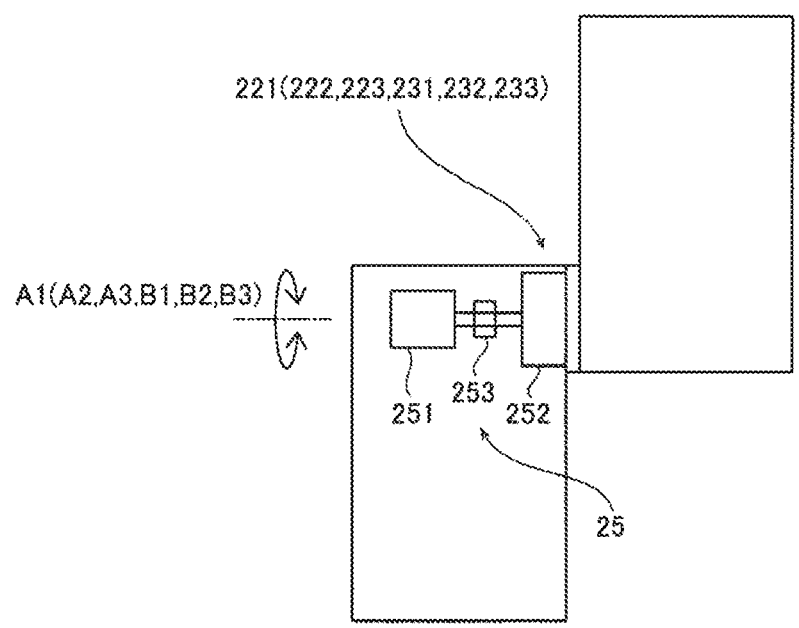
FIG. 3 is a schematic view illustrating a derive mechanism of an articulated robotic arm of the robotic operating table according to the first embodiment.

As illustrated in FIG. 3, the horizontal joints 221 to 223 and the vertical joints 231 to 233 are each driven by a drive mechanism 25. The drive mechanism 25 includes a motor 251, a reducer 252 that reduces the speed of the rotation transmitted from the motor 251 to output slower rotation, and an electromagnetic brake 253. The horizontal joints 221 to 223 and the vertical joints 231 to 233 are each rotated about the corresponding rotation axis by driving the corresponding motor 251. Also, the rotation axis of each of the horizontal joints 221 to 223 is disposed to coincide with the axis of the output rotation shaft of the corresponding reducer 252. The rotation axis of each of the vertical joints 231 to 233 is disposed to coincide with the axis of the output rotation shaft of the corresponding reducer 252.

The motor 251 includes a servomotor. The motor 251 is driven through control by the control unit 3. The reducer 252 includes a reducer such as a reducer with strain wave gearing or a reducer with eccentric oscillation-type planetary gearing, for example. In this way, the speed of rotation of the motor 251 can be effectively reduced by the small reducer 252. The electromagnetic brake 253 stops the drive of the joint.

Here, in the first embodiment, the rotation axis B1 of the vertical joint 231 is disposed along a direction that is horizontal and substantially parallel to the longitudinal direction of the table 1 (longitudinal direction: X direction). The rotation axis B2 of the vertical joint 232 is also disposed along a direction that is horizontal and substantially parallel to the longitudinal direction of the table 1 (X direction). The rotation axis B3 of the vertical joint 233 is also disposed along a direction that is horizontal and substantially parallel to the longitudinal direction of the table 1 (X direction). In other words, the rotation axes B1 to B3 of the vertical joints 231 to 233 of the vertical articulated assembly 23 are disposed along a direction that is horizontal and substantially parallel to the longitudinal direction of the table 1 (X direction).

The vertical articulated assembly 23 does not rotate about a rotation axis along the vertical direction (Z direction) relative to the table 1. In other words, the rotation axes of the vertical joints 231 to 233 of the vertical articulated assembly 23 are always substantially parallel to the horizontal direction running along the longitudinal direction of the table 1.

Figure 4:
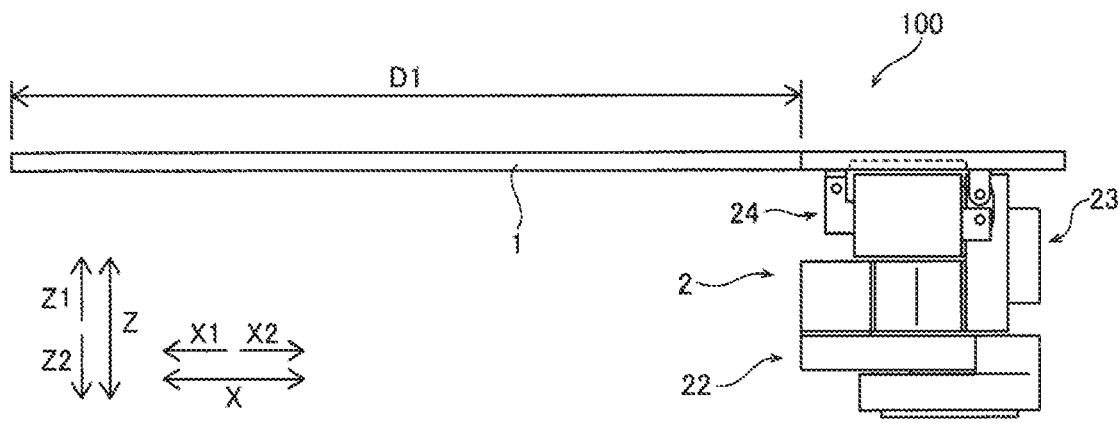
FIG. 4 is a side view for explaining the maximum imageable range of the robotic operating table according to the first embodiment.

As illustrated in FIG. 4, in the first embodiment, the radiographic imaging apparatus 300 can capture an image over a distance D1 in the X direction as its maximum imageable range with the articulated robotic arm 2 disposed folded on the X2 side of the table 1. In other words, with the articulated robotic arm 2 disposed folded on the X2 side of the table 1, a space covering the distance D1 in the X direction is left under the table 1. The distance D1 is substantially equal to the length of the radiolucent part 11 in the X direction, for example. In other words, with the robotic operating table 100 in the first embodiment, the radiographic imaging apparatus 300 can capture an image of substantially the whole body of the patient 10.

Figure 5:
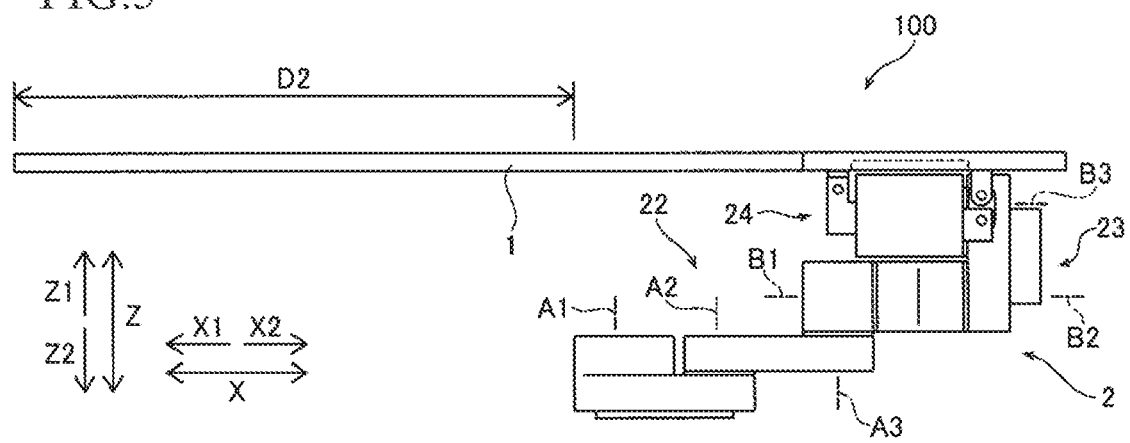
FIG. 5 is a side view for explaining the minimum imageable range of the robotic operating table according to the first embodiment.

As illustrated in FIG. 5, in the first embodiment, the radiographic imaging apparatus 300 can capture an image over a distance D2 in the X direction as its minimum imageable range with the articulated robotic arm 2 fully extended in the horizontal X2 direction. In other words, with the articulated robotic arm 2 fully extended in the horizontal X2 direction, a space covering the distance D2 in the X direction is left under the table 1. The distance D2 is longer than or equal to ½ of the length of the radiolucent part 11 in the X direction, for example. In other words, with the robotic operating table 100 in the first embodiment, the radiographic imaging apparatus 300 can capture an image of at least half of the whole body of the patient 10.

As illustrated in FIG. 2, the articulated robotic arm 2 is disposed to be completely hidden under the table 1 in the plan view (as seen from the Z direction). For example, the articulated robotic arm 2 is housed in a housing space which is a space under the table 1 when the table 1 is positioned at a surgical operation position. Specifically, the articulated robotic arm 2 is folded and completely hidden under the table 1 in the plan view (as seen from the Z direction) in a state where the articulated robotic arm 2 has moved the table 1 to a position at which to perform a surgical operation or treatment on the patient 10 placed on the table 1. Meanwhile, the length of the articulated robotic arm 2 in the folded posture in the direction parallel to the longitudinal direction of the table 1 is shorter than or equal to ½ of the length of the table 1 in the longitudinal direction.

The articulated robotic arm 2 in this embodiment can lower the table 1 down to a height of 500 mm, for example. In this way, the robotic operating table 100 can handle surgical operations which medical personnel perform while sitting on chairs. Moreover, the articulated robotic arm 2 can raise the table 1 up to a height of 1100 mm.

Also, in the first embodiment, the articulated robotic arm 2 causes the table 1 to yaw about an axis along the vertical direction (Z direction) by using at least one of the horizontal joints (at least one of 221, 222, and 223). For example, the articulated robotic arm 2 causes the table 1 to yaw by using the bottom horizontal joint 221 or the top horizontal joint 223. Alternatively, the articulated robotic arm 2 may cause the table 1 to yaw by driving two or all of the horizontal joints in conjunction with each other.

Figure 6:
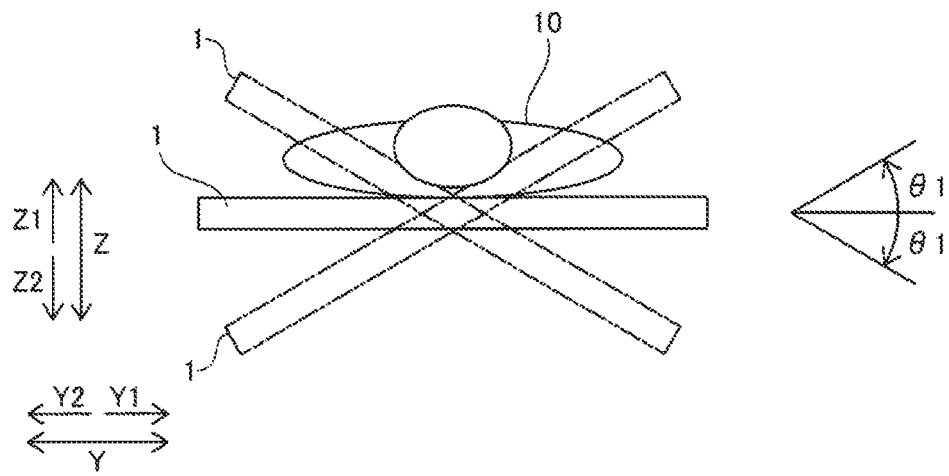
FIG. 6 is a front view for explaining roll of the robotic operating table according to the first embodiment.

Also, as illustrated in FIG. 6, the articulated robotic arm 2 causes the table 1 to roll about an axis along the longitudinal direction (X direction) by using at least one of the vertical joints (at least one of 231, 232, and 233). For example, the articulated robotic arm 2 causes the table 1 to roll by using the bottom vertical joint 231 or the top vertical joint 233. Alternatively, the articulated robotic arm 2 may cause the table 1 to roll by driving two or all of the vertical joints in conjunction with each other. In a view of the table 1 from the X direction, the articulated robotic arm 2 is capable of causing the table 1 to roll up to an angle θ1 clockwise with respect the horizontal direction and causing the table 1 to roll up to the angle θ1 counterclockwise with respect the horizontal direction. θ1 is 30 degrees, for example.

Figure 7:
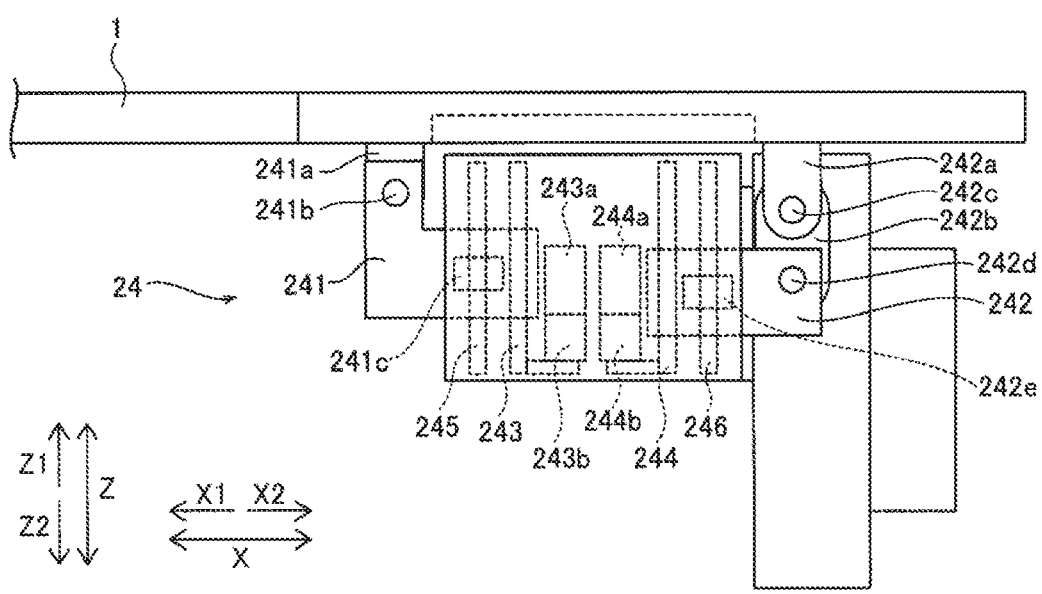
FIG. 7 is a side view illustrating a pitch mechanism of the robotic operating table according to the first embodiment.
Figure 8:
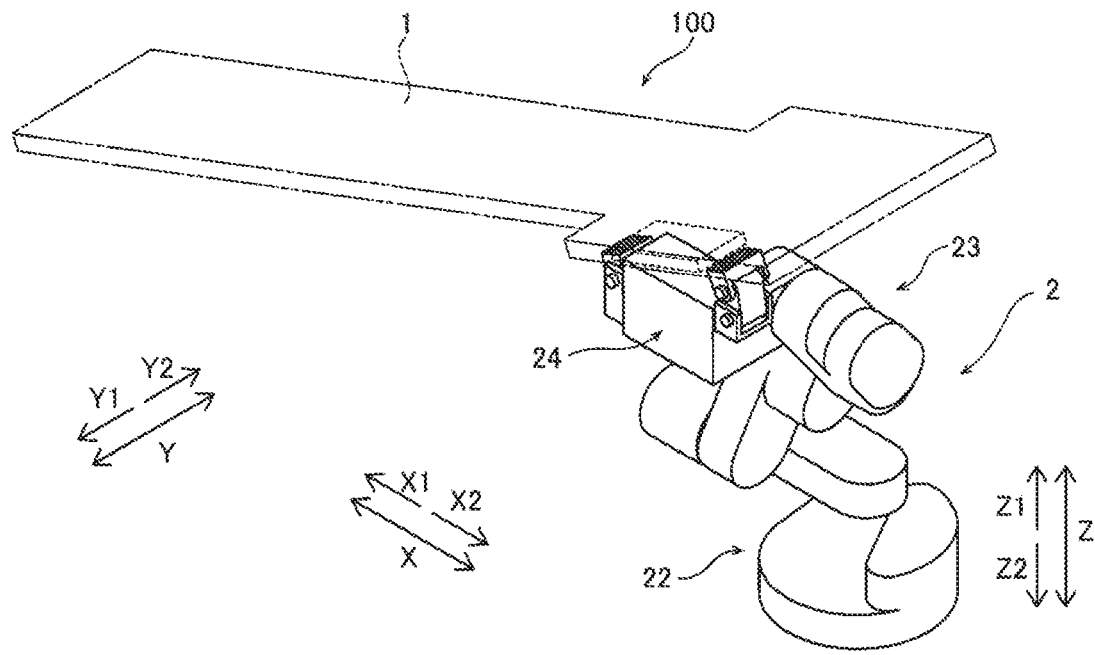
FIG. 8 is a perspective view for explaining pitch of the robotic operating table according to the first embodiment.
Figure 9:
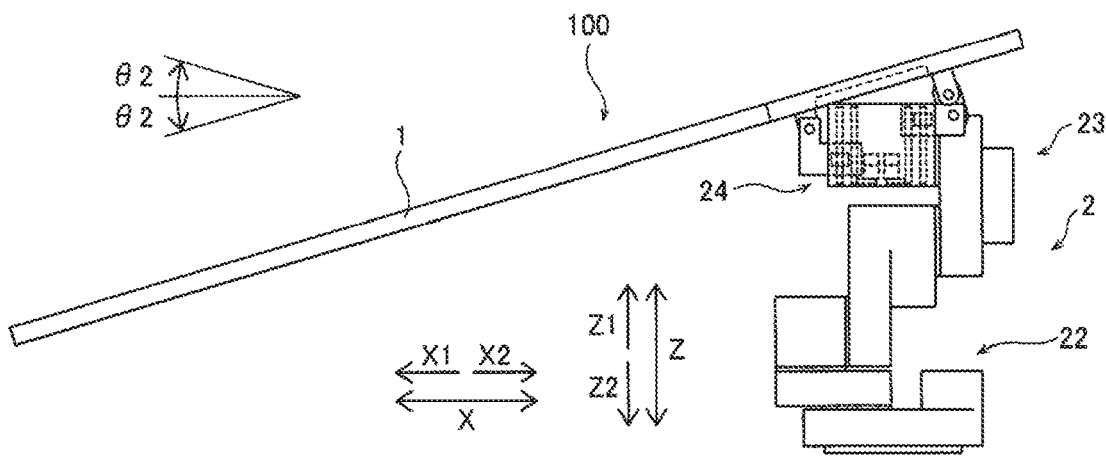
FIG. 9 is a side view for explaining the pitch of the robotic operating table according to the first embodiment.

Also, as illustrated in FIG. 8 and FIG. 9, the articulated robotic arm 2 causes the table 1 to pitch about an axis along the transverse direction (Y direction) by using the pitch mechanism 24. As illustrated in FIG. 7, the pitch mechanism 24 includes a first support member 241, a second support member 242, a first ball screw 243, a second ball screw 244, a first linear guide 245, and a second linear guide 246. The first support member 241 includes a coupling part 241a, a pivot shaft 241b, and a slider 241c. The second support member 242 includes coupling parts 242a and 242b, pivot shafts 242c and 242d, and a slider 242e. The first ball screw 243 is connected to a motor 243a through a reducer 243b. The second ball screw 244 is connected to a motor 244a through a reducer 244b.

The pitch mechanism 24 is supported on the opposite end of the vertical articulated assembly 23. The pitch mechanism 24 is connected to the table 1 and supports the table 1 such that the table 1 can pitch. Specifically, the pitch mechanism 24 supports the table 1 such that the table 1 can pitch by using the first support member 241 and the second support member 242. The first support member 241 and the second support member 242 are disposed away from each other by a predetermined distance along the direction parallel to the longitudinal direction of the table 1 (X direction). The first support member 241 is disposed on the X1 direction side. The second support member 242 is disposed on the X2 direction side. Moreover, the pitch mechanism 24 is disposed near one side of the table 1 in the transverse direction (Y direction). Specifically, the pitch mechanism 24 is disposed near the end of the table 1 in the Y1 direction.

The coupling part 241a of the first support member 241 is fixed to the table 1 and pivotally supported on the pivot shaft 241b. The first support member 241 is moved in the vertical direction (Z direction) by driving the first ball screw 243. Moreover, the first support member 241 is slidably mounted on the first linear guide 245. Specifically, the slider 241c, which is fixed to the first support member 241, is engaged with the first linear guide 245 to guide vertical movement of the first support member 241.

The coupling part 242a of the second support member 242 is fixed to the table 1 and pivotally supported on the pivot shaft 242c. The coupling part 242b is pivotally mounted on the pivot shafts 242c and 242d. The second support member 242 is moved in the vertical direction (Z direction) by driving the second ball screw 244. Moreover, the second support member 242 is slidably mounted on the second linear guide 246. Specifically, the slider 242e, which is fixed to the second support member 242, is engaged with the second linear guide 246 to guide vertical movement of the second support member 242.

The first ball screw 243 is disposed such that its shaft extends in the vertical direction (Z direction). The first ball screw 243 is engaged with the first support member 241. By driving the motor 243a, the first ball screw 243 is rotated and moves the first support member 241 in the vertical direction.

The second ball screw 244 is disposed such that its shaft extends in the vertical direction (Z direction). The second ball screw 244 is engaged with the second support member 242. By driving the motor 244a, the second ball screw 244 is rotated and moves the second support member 242 in the vertical direction.

The first linear guide 245 is disposed to extend in a direction substantially parallel to the direction of extension of the first ball screw 243. In other words, the first linear guide 245 is disposed to extend in the vertical direction (Z direction). The first linear guide 245 guides vertical movement of the first support member 241 through the slider 241c.

The second linear guide 246 is disposed to extend in a direction substantially parallel to the direction of extension of the second ball screw 244. In other words, the second linear guide 246 is disposed to extend in the vertical direction (Z direction). The second linear guide 246 guides vertical movement of the second support member 242 through the slider 242e.

As the first support member 241 is moved to a position lower than the second support member 242, the table 1 is caused to pitch such that its X1 side becomes lower. In contrast, as the first support member 241 is moved to a position higher than the second support member 242, the table 1 is caused to pitch such that its X1 side becomes higher. Also, as the first support member 241 and the second support member 242 are moved to the same height position, the table 1 is caused to pitch into a horizontal posture.

As illustrated in FIG. 9, in a view of the table 1 from the Y direction, the articulated robotic arm 2 is capable of causing the table 1 to pitch up to an angle θ2 clockwise with respect to the horizontal direction and causing the table 1 to pitch up to the angle θ2 counterclockwise with respect to the horizontal direction. θ2 is 15 degrees, for example.

The control unit 3 is installed inside the base 21 and controls the movement of the table 1 by the articulated robotic arm 2. Specifically, the control unit 3 moves the table 1 by controlling the drive of the articulated robotic arm 2 based on an operation by a medical person (operator).

The radiographic imaging apparatus 300 is capable of capturing a radiographic projection image of the patient 10 placed on the table 1. The X-ray irradiation part 301 and the X-ray detection part 302 are supported on the C-arm 303. The X-ray irradiation part 301 and the X-ray detection part 302 are moved with movement of the C-arm 303, and are positioned to face each other during radiography from opposite sides of an imaging site in the patient 10. For example, one of the X-ray irradiation part 301 and the X-ray detection part 302 is positioned in a space above the table 1 while the other is positioned in a space under the table 1. Also, during radiography, the C-arm 303, supporting the X-ray irradiation part 301 and the X-ray detection part 302, is positioned in the spaces above and under the table 1 as well.

As illustrated in FIG. 1, the X-ray irradiation part 301 is disposed to face the X-ray detection part 302. Also, the X-ray irradiation part 301 is capable of emitting X rays toward the X-ray detection part 302. The X-ray detection part 302 detects the X rays emitted by the X-ray irradiation part 301. The X-ray detection part 302 includes a flat panel detector (FPD). The X-ray detection part 302 captures a radiographic image based on the detected X rays. Specifically, the X-ray detection part 302 converts the detected X rays into electric signals and transmits them to an image processing unit (not illustrated).

The X-ray irradiation part 301 is connected to one end of the C-arm 303, and the X-ray detection part 302 is connected to the opposite end of the C-arm 303. The C-arm 303 has a substantially C-shape. In this way, the C-arm 303 can support the X-ray irradiation part 301 and the X-ray detection part 302 while extending around the table 1 and the patient 10 to avoid interfering with them during radiography. The C-arm 303 is capable of moving relative to the table 1. Specifically, the C-arm 303 is capable of moving horizontally and vertically and also rotating about a horizontal rotation axis and a vertical rotation axis to position the X-ray irradiation part 301 and the X-ray detection part 302 to desired positions relative to the patient 10 placed on the table 1. The C-arm 303 is moved by a drive part (not illustrated) based on an operation by a medical person (operator). The C-arm 303 is also manually movable by a medical person (operator).

Advantageous Effects of First Embodiment

The first embodiment can offer the following advantageous effects.

In the first embodiment, as explained above, the rotation axes of the vertical joints 231, 232, and 233 of the articulated robotic arm 2 are disposed along a direction that is horizontal and substantially parallel to the longitudinal direction of the table 1 (X direction). Here, the articulated robotic arm 2 supports the table 1 at a position near its one end in the longitudinal direction in order to prevent interference of the articulated robotic arm 2 with medical personnel and other equipment. For this reason, the distance from the supported position and the position of the center of gravity of the table 1 with the patient 10 placed thereon is longer in the longitudinal direction of the table 1 (X direction) than in the transverse direction of the table 1 (Y direction). As a result, the moment at the position of the table 1 supported by the articulated robotic arm 2 is greater about a rotation axis along the transverse direction of the table 1 than about a rotation axis along the longitudinal direction of the table 1. Thus, with the rotation axes of the vertical joints 231, 232, and 233 of the articulated robotic arm 2 disposed along a direction that is horizontal and substantially parallel to the longitudinal direction of the table 1, the moment load for supporting the table 1 is not large in the direction of rotation of the vertical joints 231, 232, and 233. To put it differently, the moment load in the longitudinal direction of the table 1 can be supported in the direction of the rotation axes of the vertical joints 231, 232, and 233, and the output of the drive mechanisms 25 for driving the vertical joints 231, 232, and 233 do not therefore need to be large. Large reducers do not need to be provided either to make the output torques of the drive mechanisms 25 large. Consequently, the vertical joints 231, 232, and 233 can be prevented from becoming large in size. This makes it possible to downsize the articulated robotic arm 2, which moves the table 1 with the patient 10 placed thereon, on whom a surgical operation is to be performed, while ensuring that the vertical joints 231, 232, and 233 of the articulated robotic arm 2 have strength to withstand loads thereon.

Also, in the first embodiment, as explained above, the articulated robotic arm 2 supports the table 1 at a position near its one end in the longitudinal direction (X direction). In this way, a space can be left under the opposite side of the table 1 from the one end side of the table 1, which is supported by the articulated robotic arm 2, and a sufficient space can therefore be left around the table 1, on which to place a patient. As a result, interference of the articulated robotic arm 2 with medical personnel and other equipment can be prevented.

Also, in the first embodiment, as explained above, the rotation axis of each of the vertical joints 231, 232, and 233 is disposed along a direction that is horizontal and substantially parallel to the longitudinal direction of the table 1 (X direction). In this way, it is possible to downsize the vertical joints 231, 232, and 233 while ensuring that the vertical joints 231, 232, and 233 have strength to withstand loads thereon.

Also, in the first embodiment, as explained above, the drive mechanisms 25 which drive the vertical joints 231, 232, and 233 are each provided with the motor 251 and the reducer 252, which outputs the rotation of the motor 251 while reducing the speed of the rotation, and the rotation axis of each of the vertical joints 231, 232, and 233 is disposed to coincide with the axis of the output rotation shaft of the corresponding reducer 252. In this way, the reducer 252 can increase the output torque of the motor 251, and the output of the motor 251 does not therefore need to be large. Moreover, since the output rotation shaft of the reducer 252 can be disposed along a direction that is horizontal and substantially parallel to the longitudinal direction of the table 1, moment loads on the reducer 252 are not large.

Also, in the first embodiment, as explained above, the articulated robotic arm 2 is provided with the horizontal articulated assembly 22, including the horizontal joints 221, 222, and 223, and the vertical articulated assembly 23, including the vertical joints 231, 232, and 233. Moreover, the one end of the horizontal articulated assembly 22 is supported on the base 21 while the opposite end of the horizontal articulated assembly 22 supports the one end of the vertical articulated assembly 23, and the opposite end of the vertical articulated assembly 23 supports the table 1. In this way, horizontal rotation of the table 1 does not occur between the vertical articulated assembly 23 and the table 1. Hence, the articulated robotic arm 2 can move the table 1 vertically and horizontally while maintaining the relation between the direction of extension of the rotation axes of the vertical joints 231, 232, and 233 and the longitudinal direction of the table 1. Moreover, the table 1 can be easily moved to a desired position in the horizontal direction by the horizontal articulated assembly 22, including the horizontal joints 221, 222, and 223. Furthermore, the table 1 can be easily moved to a desired position in the vertical direction by the vertical articulated assembly 23, including the vertical joints 231, 232, and 233. Also, the horizontal joints 221, 222, and 223 can be disposed together on the base 21 side, and the vertical joints 231, 232, and 233 can be disposed together on the table 1 side. Then, the table 1 can be moved in the horizontal direction by driving the horizontal joints 221, 222, and 223 on the base 21 side, and the table 1 can be moved in the vertical direction by driving the vertical joints 231, 232, and 233 on the table 1 side. In this way, the horizontal joints 221, 222, and 223 and the vertical joints 231, 232, and 233 do not need to be driven in conjunction with each other to move the table 1 in the horizontal direction or in the vertical direction. Accordingly, the control of drive of the articulated robotic arm 2 is less complicated than when the vertical joints 231, 232, and 233 and the horizontal joints 221, 222, and 223 are disposed alternately.

Also, in the first embodiment, as explained above, the horizontal articulated assembly 22 is provided with the three horizontal joints 221, 222, and 223, and the vertical articulated assembly 23 is provided with the three vertical joints 231, 232, and 233. Thus, considering that the horizontal articulated assembly 22 has a certain length when fully extended, the horizontal articulated assembly 22 can have short joint-to-joint distances and therefore be compact when folded and shortened as compared to a case where it is provided with one or two horizontal joints. Moreover, the horizontal articulated assembly 22 can simplify the apparatus configuration as compared to a case where it is provided with four or more horizontal joints. Considering that the vertical articulated assembly 23 has a certain length when fully extended, the vertical articulated assembly 23 can have short joint-to-joint distances and therefore be compact when folded and shortened as compared to a case where it is provided with one or two vertical joints. Moreover, the vertical articulated assembly 23 can simplify the apparatus configuration as compared to a case where it is provided with four or more vertical joints.

Also, in the first embodiment, as explained above, the articulated robotic arm 2 causes the table 1 to yaw about an axis along the vertical direction (Z direction) by using at least one of the horizontal joints (at least one of 221, 222, and 223). Thus, the table 1 can be easily caused to yaw to a desired position by using one or more horizontal joints (at least one of 221, 222, and 223) of the articulated robotic arm 2.

Also, in the first embodiment, as explained above, the articulated robotic arm 2 causes the table 1 to roll about an axis along the longitudinal direction (X direction) by using at least one of the vertical joints (at least one of 231, 232, and 233). Thus, the table 1 can be easily caused to roll to a desired rotation angle position by using one or more vertical joints (at least one of 221, 222, and 223) of the articulated robotic arm 2.

Also, in the first embodiment, as explained above, the articulated robotic arm 2 is provided with the pitch mechanism 24, which supports the table 1 and causes the table 1 to pitch about an axis along the transverse direction (Y direction). Moreover, the pitch mechanism 24 is provided with the first ball screw 243, which is disposed such that its shaft extends in the vertical direction, the second ball screw 244, which is disposed such that its shaft extends in the vertical direction, the first support member 241, which supports the table 1 and is moved in the vertical direction (Z direction) by the first ball screw 243 and, and the second support member 242, which supports the table 1 and is moved in the vertical direction (Z direction) by the second ball screw 244. Furthermore, the first support member 241 and the second support member 242 are disposed away from each other by a predetermined distance in the direction parallel to the longitudinal direction of the table 1 (X direction). In this way, the table 1 can be easily caused to pitch to a desired rotation angle position by driving the first ball screw 243 and the second ball screw 244 in conjunction with each other.

Also, in the first embodiment, as explained above, the pitch mechanism 24 is provided with the first linear guide 245, which is disposed to extend in the direction parallel to the direction of extension of the first ball screw 243, and the second linear guide 246, which is disposed to extend in the direction parallel to the direction of extension of the second ball screw 244. Moreover, the first support member 241 is slidably mounted on the first linear guide 245, and the second support member 242 is slidably mounted on the second linear guide 246. In this way, the first linear guide 245 allows accurate linear movement of the first support member 241, and the second linear guide 246 allows accurate linear movement of the second support member 242. Hence, the table 1 can be caused to pitch accurately.

Also, in the first embodiment, as explained above, the one end of the horizontal articulated assembly 22 is supported on the base 21 while the opposite end of the horizontal articulated assembly 22 supports the one end of the vertical articulated assembly 23, and the pitch mechanism 24 is supported on the opposite end of the vertical articulated assembly 23. Thus, the horizontal joints 221, 222, and 223 can be disposed together on the base 21 side, and the vertical joints 231, 232, and 233 can be disposed together on the table 1 side. Then, the table 1 can be moved in the horizontal direction by driving the horizontal joints 221, 222, and 223 on the base 21 side, and the table 1 can be moved in the vertical direction by driving the vertical joints on the table 1 side. In this way, the horizontal joints 221, 222, and 223 and the vertical joints 231, 232, and 233 do not need to be driven in conjunction with each other to move the table 1 in the horizontal direction or in the vertical direction. Accordingly, the control of drive of the articulated robotic arm 2 is less complicated than when the vertical joints and the horizontal joints are disposed alternately. Moreover, since the pitch mechanism 24 can be provided on the table 1 side of the vertical articulated assembly 23, the table 1 can be easily caused to pitch by using the pitch mechanism 24 independently of the vertical articulated assembly 23.

Also, in the first embodiment, as explained above, the table 1 is provided with the radiolucent part 11 and the support part 12, which supports the radiolucent part 11, and the opposite end of the articulated robotic arm 2 supports the support part 12 on the one end side of the table 1. Thus, by disposing the articulated robotic arm 2 on the support part 12 side to leave a sufficient space under the radiolucent part 11, the radiographic imaging apparatus 300 can be placed under the radiolucent part 11 and therefore capture a radiographic image of the patient 10 placed on the table 1.

Second Embodiment

Next, a second embodiment of the present invention is explained with reference to FIG. 10 and FIG. 11. In this second embodiment is explained an example with a configuration in which an articulated robotic arm includes a pitch mechanism including a pitch-support member unlike the above first embodiment, in which an articulated robotic arm includes a pitch mechanism including a first support member and a second support member. Note that parts similar to the first embodiment are denoted by similar reference signs.

(Configuration of Robotic Operating Table)

Figure 10:
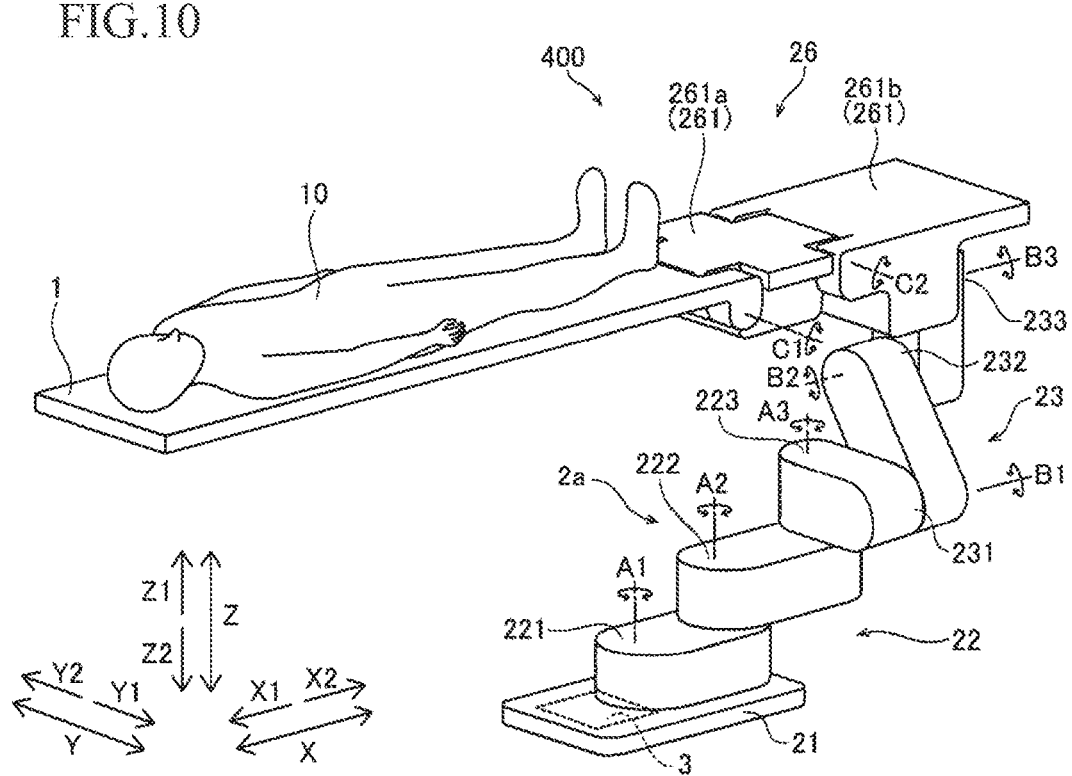
FIG. 10 is a perspective view illustrating a robotic operating table according to a second embodiment.

As illustrated in FIG. 10, a robotic operating table 400 includes a table 1 on which to place a patient, an articulated robotic arm 2a, and a control unit 3. The articulated robotic arm 2a includes a base 21, a horizontal articulated assembly 22, a vertical articulated assembly 23, and a pitch mechanism 26. The horizontal articulated assembly 22 includes horizontal joints 221, 222, and 223. The vertical articulated assembly 23 includes vertical joints 231, 232, and 233. The pitch mechanism 26 includes a pitch-support member 261.

Here, in the second embodiment, a rotation axis B1 of the vertical joint 231 is disposed along a direction that is horizontal and substantially parallel to the longitudinal direction of the table 1 (X direction). A rotation axis B2 of the vertical joint 232 is also disposed along a direction that is horizontal and substantially parallel to the longitudinal direction of the table 1 (X direction). A rotation axis B3 of the vertical joint 233 is also disposed along a direction that is horizontal and substantially parallel to the longitudinal direction of the table 1 (X direction). In other words, the rotation axes B1 to B3 of the vertical joints 231 to 233 of the vertical articulated assembly 23 are disposed along a direction that is horizontal and substantially parallel to the longitudinal direction of the table 1 (X direction).

Also, in the second embodiment, the articulated robotic arm 2 causes the table 1 to pitch about an axis along the transverse direction (Y direction) by using the pitch mechanism 26. The pitch mechanism 26 is supported on the vertical articulated assembly 23. Moreover, the pitch mechanism 26 supports the table 1. Specifically, the pitch mechanism 26 supports the table 1 at a position near its end on the X2 direction side.

The pitch-support member 261 of the pitch mechanism 26 supports one end of the table 1 such that the one end of the table 1 is rotatable about a rotation axis for pitching. Moreover, the pitch mechanism 26 includes a first pitch-support member 261*a* and a second pitch-support member 261*b*.

The first pitch-support member 261*a* supports the one end of the table 1 such that the one end of the table 1 is rotatable about a rotation axis C1 parallel to the transverse direction of the table 1. The first pitch-support member 261*a* is provided with a motor, a reducer that transmits the rotation of the motor while reducing the speed of the rotation, and an electromagnetic brake in order to cause the table 1 to pitch. The second pitch-support member 261*b* supports the first pitch-support member 261*a* such that the first pitch-support member 261*a* is rotatable about a rotation axis C2 parallel to the transverse direction of the table 1. The second pitch-support member 261*b* is provided with a motor, a reducer that transmits the rotation of the motor while reducing the speed of the rotation, and an electromagnetic brake in order to cause the first pitch-support member 261*a* to pitch.

Figure 11:
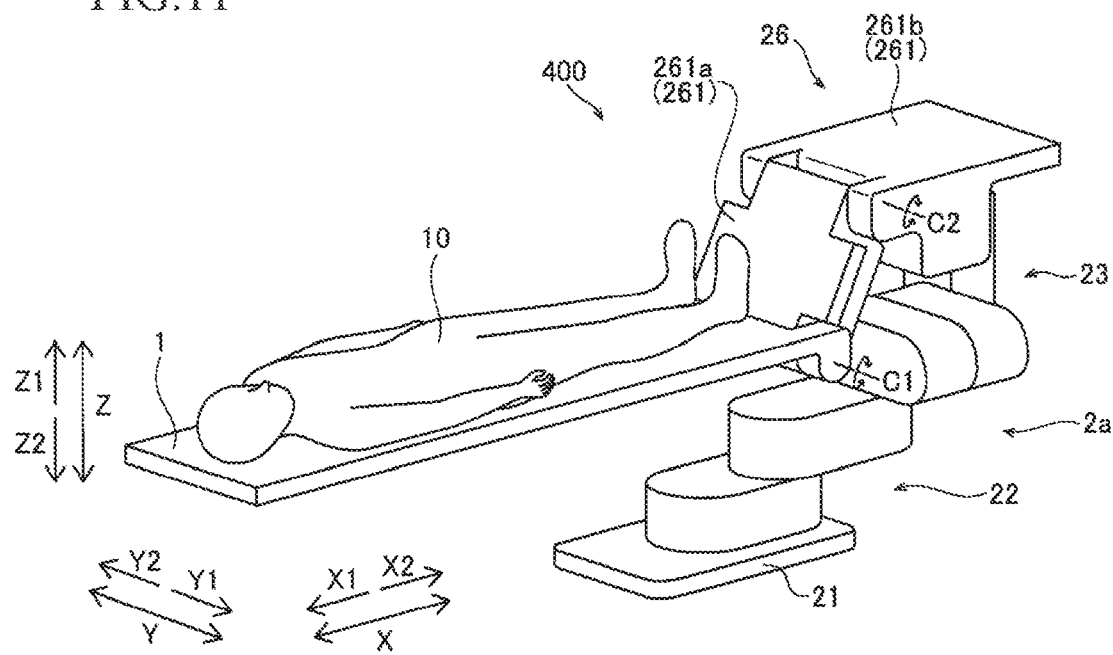
FIG. 11 is a view for explaining a pitch mechanism of the robotic operating table according to the second embodiment.

As illustrated in FIG. 11, the pitch mechanism 26 moves the table 1 downward in the vertical direction (Z2 direction) by moving the first pitch-support member 261*a* and the second pitch-support member 261*b* in conjunction with each other.

Note that the other features of the configuration in the second embodiment are similar to the above first embodiment.

Advantageous Effects of Second Embodiment

The second embodiment can offer the following advantageous effects.

As explained above, in the second embodiment, the rotation axes of the vertical joints 231, 232, and 233 of the articulated robotic arm 2*a* are disposed along a direction that is horizontal and substantially parallel to the longitudinal direction of the table 1 (X direction), as in the first embodiment. In this way, it is possible to downsize the articulated robotic arm 2*a*, which moves the table 1 with a patient 10 placed thereon on whom a surgical operation is to be performed, while ensuring that the vertical joints 231, 232, and 233 of the articulated robotic arm 2*a* have strength to withstand loads thereon.

Also, in the second embodiment, as explained above, the articulated robotic arm 2*a* is provided with the pitch mechanism 26, which supports the table 1 and causes the table 1 to pitch about an axis along the transverse direction (Y direction). Moreover, the pitch mechanism 26 is provided with the pitch-support member 261, which supports the one end of the table 1 such that the one end of the table 1 is rotatable about a rotation axis for pitching. In this way, the table 1 can be easily moved to pitch to a desired rotation angle position by using the pitch mechanism 26 while the table 1 is supported by using the pitch-support member 261.

Also, in the second embodiment, as explained above, the pitch-support member 261 of the pitch mechanism 26 includes the first pitch-support member 261*a*, supporting the one end of the table 1 such that the one end of the table 1 is rotatable about a rotation axis parallel to the transverse direction of the table 1, and the second pitch-support member 261*b*, supporting the first pitch-support member 261*a* such that the first pitch-support member 261*a* is rotatable about a rotation axis parallel to the transverse direction of the table 1. In this way, the table 1 is capable of pitching at two stages using the pitching by the first pitch-support member 261*a* and the pitching by the second pitch-support member 261*b*. Hence, the range of angles within which the table 1 can pitch can be easily made wide.

Note that the other advantageous effects of the second embodiment are similar to the above first embodiment.

Third Embodiment

Next, a third embodiment of the present invention is explained with reference to FIG. 12 to FIG. 16. In this third embodiment is explained an example with a configuration in which an articulated robotic arm includes a pitch mechanism including a link mechanism, unlike the above first embodiment, in which an articulated robotic arm includes a pitch mechanism including a first support member and a second support member. Note that parts similar to the first embodiment are denoted by similar reference signs.

(Configuration of Robotic Operating Table)

Figure 12:
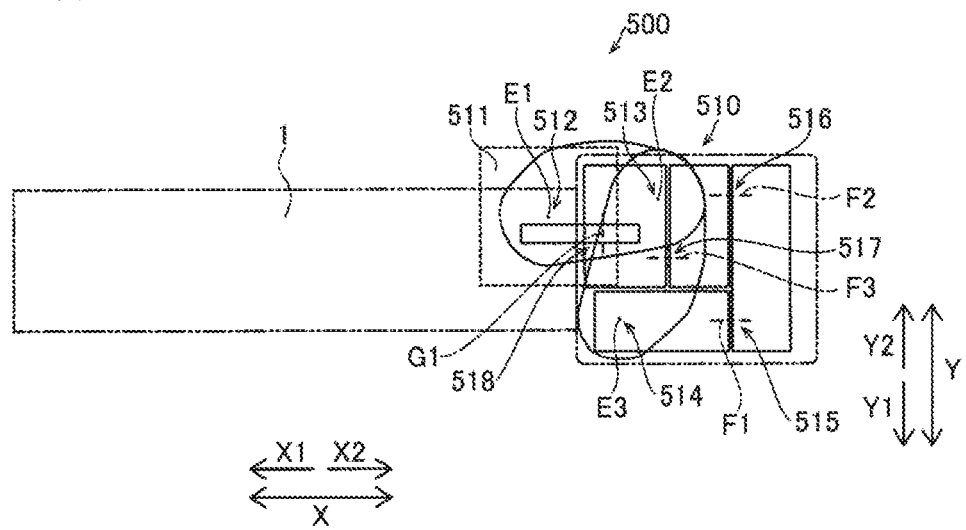
FIG. 12 is a plan view illustrating a robotic operating table according to a third embodiment.
Figure 13:
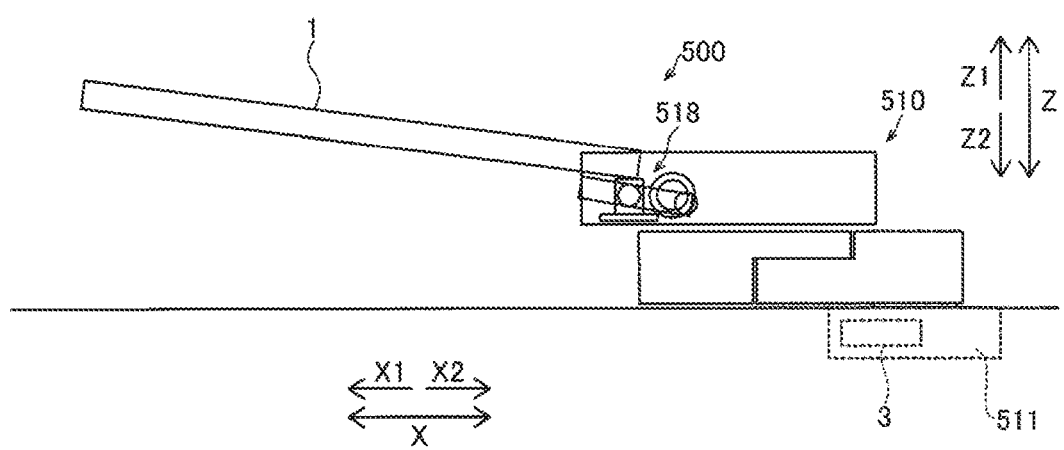
FIG. 13 is a side view illustrating the robotic operating table according to the third embodiment.

As illustrated in FIG. 12, a robotic operating table 500 includes a table 1 on which to place a patient, an articulated robotic arm 510, and a control unit 3 (see FIG. 13). The articulated robotic arm 510 includes a base 511, a horizontal articulated assembly including horizontal joints 512, 513, and 514, a vertical articulated assembly including vertical joints 515, 516, and 517, and a pitch mechanism 518.

The articulated robotic arm 510 moves the table 1 with seven degrees of freedom. Specifically, with the horizontal articulated assembly, the articulated robotic arm 510 has three degrees of freedom to rotate about a vertical rotation axis E1, rotate about a vertical rotation axis E2, and rotate about a vertical rotation axis E3. Further, with the vertical articulated assembly, the articulated robotic arm 510 has three degrees of freedom to rotate about a horizontal rotation axis F1, rotate about a horizontal rotation axis F2, and rotate about a horizontal rotation axis F3. Furthermore, with the pitch mechanism 518, the articulated robotic arm 510 has one degree of freedom to allow the table 1 to pitch about a rotation axis along its transverse direction (Y direction) (see FIG. 13).

Here, in the third embodiment, the rotation axis F1 of the vertical joint 515 is disposed along a direction that is horizontal and substantially parallel to the longitudinal direction of the table 1 (X direction). The rotation axis F2 of the vertical joint 516 is also disposed along a direction that is horizontal and substantially parallel to the longitudinal direction of the table 1 (X direction). The rotation axis F3 of the vertical joint 517 is also disposed along a direction that is horizontal and substantially parallel to the longitudinal direction of the table 1 (X direction). In other words, the rotation axes F1 to F3 of the vertical joints 515 to 517 of the vertical articulated assembly are disposed along a direction that is horizontal and substantially parallel to the longitudinal direction of the table 1 (X direction).

Also, in the third embodiment, the articulated robotic arm 510 causes the table 1 to pitch about an axis along the transverse direction (Y direction) by using the pitch mechanism 518. The pitch mechanism 518 is supported on the vertical articulated assembly. Moreover, the pitch mechanism 518 supports the table 1. Specifically, the pitch mechanism 518 supports the table 1 at a position near its end on the X2 direction side.

Figure 14:
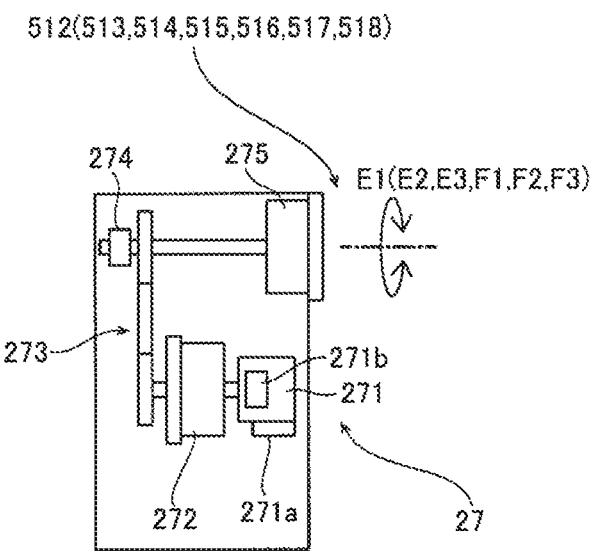
FIG. 14 is a schematic view illustrating a derive mechanism of an articulated robotic arm of the robotic operating table according to the third embodiment.

As illustrated in FIG. 14, the horizontal joints 512 to 514, the vertical joints 515 to 517, and the pitch mechanism 518 are each driven by a drive mechanism 27. The drive mechanism 27 includes a motor 271, a first reducer 272 that outputs the rotation of the motor 271 while reducing the speed of the rotation, and a second reducer 275 that outputs the rotation of the first reducer 272 while reducing the speed of the rotation. The drive mechanism 27 further includes gearing 273 and an electromagnetic brake 274.

Also, the motor 271 includes an encoder 271a and an incorporated electromagnetic brake 271b. Further, the electromagnetic brake 274 is mounted on a rotation shaft of the second reducer 275. The electromagnetic brakes 271b and 274 brake the joint. The encoder 271a detects the amount of drive of the motor 271 and transmits the result of the detection to the control unit 3. The rotation axis of each of the horizontal joints 512 to 514 is disposed to coincide with the axis of the output rotation shaft of the corresponding second reducer 275. The rotation axis of each of the vertical joints 515 to 517 is disposed to coincide with the axis of the output rotation shaft of the corresponding second reducer 275.

The motor 271 includes a servomotor. The motor 271 is driven through control by the control unit 3. The first reducer 272 and the second reducer 275 each include a reducer such as a reducer with strain wave gearing or a reducer with eccentric oscillation-type planetary gearing, for example. Note that the horizontal joints 512 to 514 may each include a single reducer as illustrated in FIG. 3.

Figure 15:
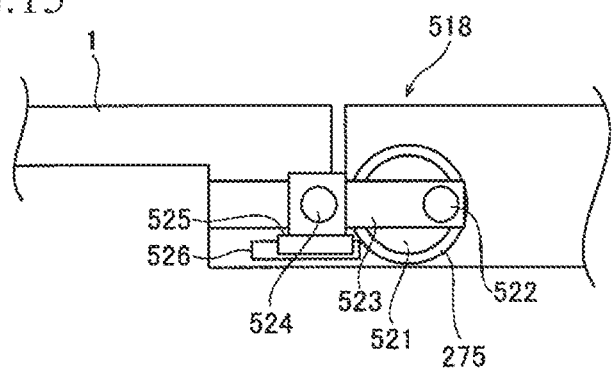
FIG. 15 is a first view for explaining a pitch mechanism of the robotic operating table according to the third embodiment.
Figure 16:
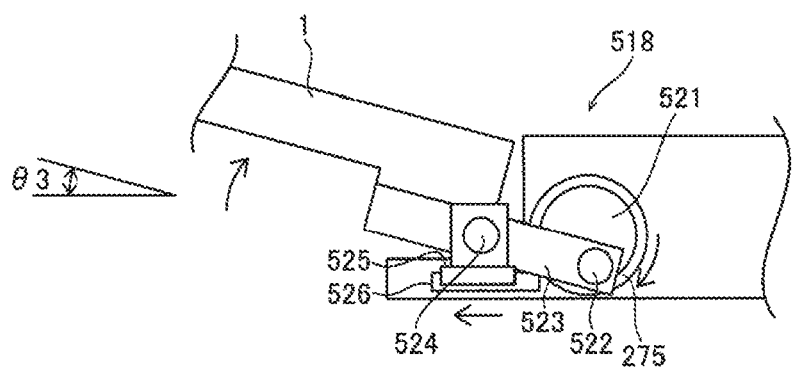
FIG. 16 is a second view for explaining the pitch mechanism of the robotic operating table according to the third embodiment.

As illustrated in FIG. 15, the pitch mechanism 518 supports one end of the table 1 such that the one end of the table 1 is rotatable about a rotation axis for pitching. Moreover, the pitch mechanism 518 includes a link mechanism including a rotary part 521, a pivot 522, a link 523, a pivot 524, a slider 525, and a rail 526. As illustrated in FIG. 15 and FIG. 16, the pitch mechanism 518 is capable of causing the table 1 to pitch up to an angle of θ3 with respect to the horizontal direction as seen from the Y direction.

The rotary part 521 is connected to the output rotation shaft of the second reducer 275 of one of the drive mechanisms 27 and rotates about the rotation axis. The link 523 is connected to the rotary part 521 through the pivot 522. The pivot 522 is connected to the rotary part 521 with a predetermined distance left between the pivot 522 and the center line of rotation of the rotary part 521. Thus, the pivot 522 moves in the circumferential direction of the rotary part 521 as the rotary part 521 rotates.

Also, the slider 525 is connected to the table 1 side of the link 523 through the pivot 524. The slider 525 is capable of moving horizontally along the rail 526. Moreover, the link 523 is connected to the table 1 to support the one end of the table 1. Thus, the table 1 is caused to pitch as the link 523 tilts with respect to the horizontal direction.

As illustrated in FIG. 16, as the rotary part 521 rotates clockwise, the pivot 522 is caused to revolve such that the end of the link 523 on the pivot 522 side is moved downward. Hence, the slider 525, connected to the pivot 524, is moved toward the table 1 side and the end of the link 523 on the table 1 side is moved upward. As a result, the table 1, connected to the link 523, is caused to pitch clockwise, as illustrated in FIG. 16. Similarly, the table 1 is caused to pitch counterclockwise by rotating the rotary part 521 counterclockwise.

Note that the other features of the configuration in the third embodiment are similar to the above first embodiment.

Advantageous Effects of Third Embodiment

The third embodiment can offer the following advantageous effects.

As explained above, in the third embodiment, the rotation axes of the vertical joints 515, 516, and 517 of the articulated robotic arm 510 are disposed along a direction that is horizontal and substantially parallel to the longitudinal direction of the table 1 (X direction), as in the first embodiment. In this way, it is possible to downsize the articulated robotic arm 510, which moves the table 1 with a patient 10 placed thereon on whom a surgical operation is to be performed, while ensuring that the vertical joints 515, 516, and 517 of the articulated robotic arm 510 have strength to withstand loads thereon.

Also, in the third embodiment, as explained above, each drive mechanism 27 is provided with the motor 271, the first reducer 272, which outputs the rotation of the motor 271 while reducing the speed of the rotation, and the second reducer 275, which outputs the rotation of the first reducer 272 while reducing the speed of the rotation. Moreover, the rotation axis of each of the vertical joints 515, 516, and 517 is disposed to coincide with the axis of the output rotation shaft of the corresponding second reducer 275. In this way, the speed of rotation can be reduced at two stages by the first reducer 272 and the second reducer 275. Thus, the output torque of the motor 271 of each of the vertical joints 515, 516, and 517 can be effectively increased. As a result, the maximum output of the motor 271 can be small, thereby allowing downsizing of the motor 271 of each of the vertical joints 515, 516, and 517.

Note that the other advantageous effects of the third embodiment are similar to the above first embodiment.

Modifications

Note that the embodiment disclosed this time should be considered exemplary in all aspects and not limiting. The scope of the present invention is indicated by the claims rather than the explanation of the above embodiment and also embraces all changes that come within the meaning and range of equivalents of the claims.

For example, although the example with a hybrid operating system including a radiographic imaging apparatus provided in the hybrid operating system together with a robotic operating table has been presented in the above first to third embodiments, the present invention is not limited to this example. In the present invention, a magnetic resonance imaging apparatus that captures a magnetic resonance image of a patient may be provided in the hybrid operating system together with a robotic operating table. Note that both a radiographic imaging apparatus and a magnetic resonance imaging apparatus may be provided in the hybrid operating system together with a robotic operating table.

Also, although the example with the configuration in which a single radiographic imaging apparatus is provided in the hybrid operating system has been presented in the above first to third embodiments, the present invention is not limited to this example. In the present invention, multiple radiographic imaging apparatuses may be provided in the hybrid operating system.

Also, although the example with the configuration in which the horizontal articulated assembly includes three horizontal joints has been presented in the above first to third embodiments, the present invention is not limited to this example. In the present invention, the horizontal articulated assembly may include one or two horizontal joints or include four or more horizontal joints.

Also, although the example with the configuration in which the vertical articulated assembly includes three vertical joints has been presented in the above first to third embodiments, the present invention is not limited to this example. In the present invention, the vertical articulated assembly may include one or two vertical joints or include four or more vertical joints.

Also, although the example with the configuration in which the horizontal joints and the vertical joints each include a servomotor, a reducer, and an electromagnetic brake has been presented in the above first and second embodiments, the present invention is not limited to this example. In the present invention, each joint may include a servomotor incorporating a first electromagnetic brake, a first reducer, a second reducer, and a second electromagnetic brake mounted on a rotation shaft of the second reducer. Then, the horizontal joints and the vertical joints may each be rotated about the corresponding rotation axis by driving the corresponding servomotor. With this configuration, the drive torque of each joint can be large, and also the safety of each joint can be improved.

Also, each horizontal joint may be driven through a single reducer, and each vertical joint may be driven through multiple reducers.

Also, although the example with the configuration in which the articulated robotic arm has seven degrees of freedom has been presented in the above first to third embodiments, the present invention is not limited to this example. In the present invention, the robotic arm may have six or fewer degrees of freedom or have eight or more degrees of freedom.

Also, although the example with a C-arm radiographic imaging apparatus including an X-ray irradiation part and an X-ray detection part supported on a C-arm has been presented in the above first to third embodiments, the present invention is not limited to this example. In the present invention, for example, the radiographic imaging apparatus may include an X-ray irradiation part and an X-ray detection part disposed and supported to face each other in the vertical direction.

The above-described aspects may be combined with each other as practicable within the contemplated scope of embodiments. The above described embodiments are to be considered in all respects as illustrative, and not restrictive. The illustrated and described embodiments may be extended to encompass other embodiments in addition to those specifically described above without departing from the intended scope of the invention. The scope of the invention is to be determined by the appended claims when read in light of the specification including equivalents, rather than solely by the foregoing description. Thus, all configurations including configurations that fall within equivalent arrangements of the claims are intended to be embraced in the invention.

The invention claimed is:

1. An operating table comprising:
   a table on which to place a patient;
   a base buried or fixed to a floor; and
   an articulated robotic arm including a first end supported on the base and a second end supporting the table,
   wherein
   the robotic arm includes a vertical articulated assembly including one or more vertical joints and a horizontal articulated assembly including one or more horizontal joints, and
   the operating table is configured such that the vertical articulated assembly cannot rotate about a rotational axis extending through the vertical articulated assembly relative to the table along a vertical direction in such a manner that a rotation axis of each of the one or more vertical joints always extends along a direction that is substantially parallel to a longitudinal direction of the table in a plan view.

2. The operating table according to claim 1, wherein the articulated robotic arm supports the table at a position near a first end in the longitudinal direction of the table.

3. The operating table according to claim 1, wherein
   the robotic arm further includes a drive mechanism that drives each vertical joint,
   the drive mechanism includes a motor and a reducer that reduces speed of rotation transmitted from the motor, and
   the rotation axis of each vertical joint is positioned to coincide with an axis of an output rotation shaft of the reducer.

4. The operating table according to claim 1, wherein
   the robotic arm further includes a drive mechanism that drives each vertical joint,
   the drive mechanism includes a motor, a first reducer that reduces speed of rotation transmitted from the motor, and a second reducer that reduces speed of rotation transmitted from the first reducer, and
   the rotation axis of each vertical joint is positioned to coincide with an axis of an output rotation shaft of the second reducer.

5. The operating table according to claim 1, wherein
   a first end of the horizontal articulated assembly is supported on the base and a second end of the horizontal articulated assembly supports a first end of the vertical articulated assembly, and
   a second end of the vertical articulated assembly supports the table.

6. The operating table according to claim 5, wherein the horizontal articulated assembly includes three horizontal joints, and the vertical articulated assembly includes three vertical joints.

7. The operating table according to claim 5, wherein the robotic arm causes the table to yaw about an axis along a vertical direction.

8. The operating table according to claim 1, wherein the robotic arm causes the table to roll about an axis along the longitudinal direction.

9. The operating table according to claim 1, wherein the robotic arm includes a pitch mechanism that supports the table and causes the table to pitch.

10. The operating table according to claim 9, wherein
    the pitch mechanism includes a first ball screw arranged such that a shaft thereof extends in a vertical direction, a second ball screw that is positioned such that a shaft thereof extends in the vertical direction, a first support member that supports the table and is moved in the vertical direction by the first ball screw, and a second support member that supports the table and is moved in the vertical direction by the second ball screw, and the first support member and the second support member are positioned away from each other by a predetermined distance in a direction parallel to the longitudinal direction of the table.

11. The operating table according to claim 10, wherein the pitch mechanism further includes a first linear guide disposed to extend in a direction parallel to a direction of extension of the first ball screw, and a second linear guide disposed to extend in a direction parallel to a direction of extension of the second ball screw, the first support member is slidably mounted on the first linear guide, and the second support member is slidably mounted on the second linear guide.

12. The operating table according to claim 9, wherein the pitch mechanism includes a pitch-support member supporting a first end of the table such that the first end of the table is rotatable about a rotation axis along a transverse direction of the table.

13. The operating table according to claim 9, wherein a first end of the horizontal articulated assembly is supported on the base and a second end of the horizontal articulated assembly supports a first end of the vertical articulated assembly, and the pitch mechanism is supported on a second end of the vertical articulated assembly.

14. The operating table according to claim 1, wherein the table includes a radiolucent part and a support part supporting the radiolucent part, and the second end of the robotic arm supports the support part, which is situated on a first end side of the table.

15. The operating table according to claim 1, wherein the robotic arm is supported on the base such that the robotic arm is rotatable about an axis along a vertical direction.

16. A hybrid operating system comprising:

at least one imaging apparatus selected from a radiographic imaging apparatus that captures a radiographic projection image and a magnetic resonance imaging apparatus that captures a magnetic resonance image; and the operating table according to claim 1.

* * * * *